US006544751B1

(12) United States Patent
Brandwein et al.

(10) Patent No.: US 6,544,751 B1
(45) Date of Patent: Apr. 8, 2003

(54) METHODS OF HARVESTING RARE CELLS FROM BLOOD PRODUCTS

(75) Inventors: Harvey Brandwein, Roslyn Heights, NY (US); Samuel Coker, Dix Hills, NY (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/402,158

(22) PCT Filed: Apr. 3, 1998

(86) PCT No.: PCT/US98/06643

§ 371 (c)(1),
(2), (4) Date: Sep. 30, 1999

(87) PCT Pub. No.: WO98/45413

PCT Pub. Date: Oct. 15, 1998

Related U.S. Application Data

(60) Provisional application No. 60/043,200, filed on Apr. 8, 1997, provisional application No. 60/064,111, filed on Nov. 3, 1997, and provisional application No. 60/064,192, filed on Nov. 4, 1997.

(51) Int. Cl.[7] ............................................. G01N 33/53
(52) U.S. Cl. .................. 435/7.1; 435/455; 435/325; 435/2; 435/378; 436/519; 436/520; 436/536; 436/537; 204/183.2; 210/806; 210/793; 210/678; 424/93.7
(58) Field of Search .................. 204/183.2; 435/7.1, 435/455, 325, 2, 378; 436/519, 520, 536, 537; 210/806, 793, 678; 424/93.7

(56) References Cited

U.S. PATENT DOCUMENTS

| | | | | |
|---|---|---|---|---|
| 4,070,243 A | * | 1/1978 | Teodorescu et al. .......... | 195/79 |
| 4,255,267 A | * | 3/1981 | Hoehn et al. ................ | 210/678 |
| 4,330,410 A | | 5/1982 | Takenaka et al. | |
| 4,500,509 A | * | 2/1985 | Kass .............................. | 424/3 |
| 4,645,738 A | * | 2/1987 | Knowles et al. ................ | 435/7 |
| 4,714,680 A | | 12/1987 | Civin | |
| 4,923,620 A | | 5/1990 | Pall | |
| 4,965,204 A | | 10/1990 | Civin | |
| 5,258,126 A | | 11/1993 | Pall et al. | |
| 5,266,209 A | | 11/1993 | Knight et al. | |
| 5,432,054 A | * | 7/1995 | Saunders et al. ................ | 435/2 |
| 5,662,813 A | * | 9/1997 | Sammons et al. .......... | 210/806 |
| 5,676,849 A | * | 10/1997 | Sammons et al. .......... | 210/806 |
| 5,677,136 A | * | 10/1997 | Simmons et al. .......... | 435/7.24 |
| 5,789,148 A | * | 8/1998 | Van Vlasselaer et al. ....... | 435/2 |
| 5,814,440 A | * | 9/1998 | Hill et al. ...................... | 435/2 |
| 5,830,359 A | | 11/1998 | Knight et al. | |
| 5,871,747 A | * | 2/1999 | Gengoux-Sedlik et al. ...................... | 424/208.1 |
| 5,891,443 A | * | 4/1999 | Kogut et al. ............. | 424/204.1 |
| 5,912,177 A | * | 6/1999 | Turner et al. ................ | 435/455 |
| 5,948,278 A | * | 9/1999 | Sammons et al. .......... | 210/806 |
| 5,972,627 A | * | 10/1999 | Galy ......................... | 435/7.21 |
| 5,989,441 A | * | 11/1999 | Rashidbaigi et al. ....... | 210/793 |
| 6,001,647 A | * | 12/1999 | Peck et al. .................. | 435/325 |
| 6,015,554 A | * | 1/2000 | Galy ........................... | 424/93.7 |
| 6,087,113 A | * | 7/2000 | Caplan et al. ................ | 435/7.1 |
| 6,120,474 A | | 9/2000 | Okuda et al. | |
| 6,139,757 A | * | 10/2000 | Ohmura et al. .............. | 210/797 |
| 6,194,204 B1 | * | 2/2001 | Crawford et al. ........... | 435/372 |
| 6,268,119 B1 | * | 7/2001 | Sumita et al. .................. | 435/2 |

FOREIGN PATENT DOCUMENTS

| | | | |
|---|---|---|---|
| EP | 0397403 | 11/1990 | |
| EP | 0406485 | 1/1991 | |
| JP | 57-145662 | 9/1982 | |
| JP | 63-127765 | 5/1988 | |
| JP | 8-104643 | 4/1996 | |
| JP | 2001-161352 | 5/2001 | |
| WO | WO 94/17894 | 8/1994 | |
| WO | 94/25873 | * 11/1994 | .......... G01N/33/53 |
| WO | WO 95/17236 | 6/1995 | |
| WO | 9600782 | * 1/1996 | |
| WO | WO 96/07097 | 3/1996 | |
| WO | WO 96/11738 | 4/1996 | |
| WO | WO 97/21488 | 6/1997 | |
| WO | 97/30354 | * 8/1997 | ......... G01N/33/569 |

OTHER PUBLICATIONS

Matsumoto, U et al, Journal of Chromatography, vol. 504, apges 69–78, 1990.*
Toki, H et al, ACTA Med. Okayama, vol. 31, apges 271–273, 1977.*
Link, H et al, Blood, Oct. 1, 1995, vol. 86(7), pp. 2500–2508.*
Barr, RD et al, Scand. J. Haematol, vol. 17, pp. 300–304, 1976.*
Eisen, SA et al, Immunological communication, vol. 1(6), apges 571–577, 1972.*
Grigg, A et al, Leukemia and Lymphoma, vol. 18, pp. 329–334.*
Laboureau, E et al, Journal of Chromatography B, vol. 680, pp. 189–195, 1996.*
Lillevang et al.; "A method for isolating granulocytes from rabbit blood without causing activation", *J. of Immunological Methods*, vol. 169 (1994) pp. 137–138.
McCarthy et al.; "Granulocytic cryopreservation: further studies on the pathogenesis of impaired cellular function", *British Journal of Haematology*, 1984, vol. 56, pp. 45–54.
Syrjälä, Martti T.; "Labelling of granulocytes with radioindium: Cell isolation and labelling parameters", *Scand. J. Haematol.*, vol. 35, pp. 579–583.

(List continued on next page.)

*Primary Examiner*—Lynette R. F. Smith
*Assistant Examiner*—Ginny Allen Portner
(74) *Attorney, Agent, or Firm*—Leydig, Voit & Mayer, Ltd.

(57) ABSTRACT

The present invention provides methods of harvesting rare cells from blood products and/or obtaining products of the rare cells. The method includes contacting a blood product containing rare cells with a porous medium, and selectively retaining rare cells of interest on the porous medium. The porous medium can be contacted with an elution fluid wherein a population of the rare cells is eluted from the porous medium. Rare cells selectively retained on the porous medium can be cultured on the porous medium, and products of the rare cells can be obtained.

52 Claims, No Drawings

OTHER PUBLICATIONS

Boyum, A.; "Isolation of Lymphocytes, Granulocytes and Macrophages", *Scan. J. Immunol.*, vol. 5, Suppl. 5, 1976, pp. 9–15.

Goldman et al.; "Removal of Buffy Coat from Stored ACD Blood by Dextran Agglomeration and Subsequent Filtration", *Vox Sang*, vol. 25 (1973), pp. 470–473.

Martin et al.; "Purification of haemopoietic progenitor . . . gradients and elutriation", *British J. of Haematology*, 1986, vol. 63, pp. 187–198.

Pietersz et al.; "Comparison of Five Different Filters for the Removal of Leukocytes from Red Cell Concentrates", *Vox Sang*, 1992; vol. 62, pp. 76–81.

Muylle et al.; "Effect of Prestorage Leukocyte Removal on the Cytokine Levels in Stored Platelet Concentrates", *Vox Sang*, 1994, vol. 66, pp. 14–17.

Snyder et al.; "Effect of Microaggregate Blood Filtration on Platelet Concentrates In Vitro", *Transfusion*, vol. 21, No. 4, Jul.–Aug. 1981, pp. 427–434.

Zierdt, Charles H.; Adherence of Bacteria, Yeast, Blood Cells, and Latex Spheres to Large–Porosity Membrane Filters, *Applied and Environmental Microbiology*, vol. 38, No. 5, Dec. 1979, pp. 1166–1172.

Ferrante et al.; "Optimal Conditions for . . . Hypaque–Ficoll Method", *J. of Immunological Methods*, vol. 36 (1980), pp. 109–117.

Chong et al.; "Recovery of Human Leukocytes from a Leukocyte–Depletion Filter", *J. Transfusion*, vol. 32, No. 85, Oct. 1992 (Suppl.).

Longley et al.; "Recovery of functional human lymphocytes from Leukotrap Filters", *J. of Immunological Methods*, vol. 121 (1999), pp. 33–38.

Fliedner et al.; "Normal Granulocyte Collection with a Modified Repetitive Cycle Filtration Leukapheresis", *Blut*, vol. 29, (1974), pp. 265–276.

Steneker et al.; "Histologic and immunohistochemical . . . different polyester filters", *Transfusion*, vol. 31, No. 1, 1991, pp. 40–46.

Absolom et al.; "Elution of Human Granulocytes from Nylon Fibers by Means of Repulsive van der Waals Forces", *Transfusion*, Nov.–Dec. 1981, pp. 663–674.

Higby et al.; "Filtration Leukapheresis for Granulocyte Transfusion Therapy", *N. England J. of Medicine*, vol. 292, No. 15, Apr. 10, 1975, pp. 761–766.

Silvani et al.; "Modifications of granulocyte subpopulations and of their adherence property during filtration leukapheresis in man", *British J. of Haematology*, vol. 53, 1983, pp. 43–48.

Djerassi et al.; "Problems and Solutions With Filtration Leukapheresis", *The Granulocyte: Function and Clinical Utilization*, 1997, pp. 305–313.

Iacone et al.; "Improved Collection of Granulocytes by Modified Continuous Flow Filtration Leukapheresis Technique", *Haematologica*, vol. 65, No. 5, Dec. 1980, pp. 755–768.

Fearnley, D. B. et al., *Blood*, 93(2), 728–736 (1999).

Urban, B. C. et al., *Blood*, 98(9), 2859–1261 (2001).

* cited by examiner

METHODS OF HARVESTING RARE CELLS FROM BLOOD PRODUCTS

This application is a 35 U.S.C. 371 of PCT/US98/06643 filed Apr. 3, 1998. This application claims the benefit of U.S. Provisional Applications No. 60/043,200, filed Apr. 8, 1997; 60/064,111, filed Nov. 3, 1997; and Ser. No. 60/064,192, filed Nov. 4, 1997, which are incorporated by reference in their entireties.

TECHNICAL FIELD OF THE INVENTION

The present invention relates to harvesting rare cells from blood products and/or obtaining products of the rare cells.

BACKGROUND OF THE INVENTION

Blood is a complex biological tissue comprising a solution, suspended particulate macromolecules, and a wide variety of cell types. Blood is routinely collected from donors and typically separated into component fractions (e.g., packed red cells (PRC), platelet concentrate (PC), and plasma), and fractions such as plasma can be further processed. The component fractions are typically used to produce transfusion products.

Donated blood or component fractions can be filtered in order to separate leukocytes from the blood product, since transfusion of leukocytes can cause undesirable effects in the recipient. For example, certain leukocytes (e.g., granulocytes) which mediate immune response by distinguishing between "self" and "non-self" matter are also responsible for "graft versus host" (GVH) disease in which transfused leukocytes attack the host, often causing substantial damage to various host tissues. As the onset of GVH greatly complicates blood transfusions even between related individuals, efficient means for filtering such cells have been developed in order to minimize this risk.

As a cell fraction, leukocytes represent a disparate grouping of rare cell types. Granulocytes (e.g., neutrophils, basophils, eosinophils, etc.), monocytes, macrophages, and the like are generally phagocytotic and capable, at varying degrees, of amoeboid movement. These cell types represent the majority of rare cells (about 60–80%). These amoeboid cells can be activated by the presence of certain hormones (e.g., bacterial toxins, cytokines (notably interleukin IL-2), products of the complement complex (notably C3a, C4a, and C5a), hormone activating factors, etc.), and these cells exhibit chemotaxic movement along concentration gradients of activating factors. Thus, while blood-borne, these amoeboid cells are often localized in the sites of inflammation, infection, or injury outside of blood vessels, having left the blood vessels by the processes of diapedesis and migration in response to chemotaxic stimuli. Granulocytes isolate and/or destroy "foreign" matter, and granulocytes also present antigens to lymphocytes. Other rare cells, (e.g., lymphocytes, dendritic cells, and stem cells) are distinguishable from the amoeboid leukocytes such as granulocytes.

Donated blood represents a potential source of rare cells for clinical use and further study. However, methods for routinely and economically harvesting rare cells from blood products are generally lacking or are problematic. For example, rare cells are often isolated indiscriminately or with low efficiency. Furthermore, methods for preferentially isolating a given population of cells primarily confined to one given population (e.g., filtration leukapheresis of granulocytes) are often undesirable in certain applications. The inability to preferentially isolate some types of lymphocytes (e.g., cells that produce interferon, lymphokines, hormones, and other factors) is a particular problem, since recombinantly produced factors are often inferior in quality, or difficult and/or expensive to purify.

In view of the foregoing problems, there exists a need for an improved method for harvesting rare cells from blood products. The present invention provides such a method for harvesting rare cells from blood products. The present inventive method further provides for the isolation or separation of sub-populations of rare cells, and it affords the ability to culture a population of rare cells in order to obtain products of rare cells.

SUMMARY OF THE INVENTION

The present invention provides a method of harvesting rare cells from blood products. The method involves first contacting a blood product containing rare cells with a porous medium and selectively retaining rare cells of interest on the porous medium. Subsequently, the porous medium is contacted with an elution fluid to elute a population of the rare cells from the porous medium. In some embodiments, the method involves selectively eluting a first population of rare cells and retaining a second population of rare cells on the porous medium.

Embodiments of the method include obtaining products of rare cells selectively retained on the porous medium by contacting the porous medium containing the rare cells of interest with a nutrient-rich culture solution such that a population of the rare cells is cultured on the porous medium. The products of the rare cells thereafter can be isolated from the culture solution.

The present invention provides rare cells (or any sub-population thereof), or the products produced by such rare cells, for a variety of uses, e.g., for further study, or for clinical or academic uses. Embodiments of the present invention further provide, develop, or facilitate means of assaying activity, number, cell type, concentration, viability, filterability, secretory or metabolic activity, or other parameters relating to rare cells. Additionally, embodiments of the present inventive method provide for developing methods for testing the efficiency of leukodepletion of blood products or depletion of sub-populations of rare cells. These and other advantages of the present invention, as well as additional inventive features, will be apparent from the description of the invention provided herein.

SPECIFIC DESCRIPTION OF THE INVENTION

Definitions

As used herein, including the claims appended hereto, the following terms are defined as follows:

Rare cells are cells in blood products; generally rare cells are blood cells other than erythrocytes or platelets, e.g., leukocytes. Rare cells can be unspecialized cells such as stem cells, or specialized cells, e.g., types of leukocytes such as lymphocytes (including classes of lymphocytes such as T cells and B cells) and dendritic cells.

Blood product is a composition, any component of which (and preferably all of which) is derived from blood. Thus, blood product can be whole blood; however, the blood product also can be any fraction thereof (e.g., plasma, packed red cells, buffy coat, a concentrated suspension of cells in a solution, especially a product including rare cells).

A particulate is retained on a porous medium if the porous medium acts as a substrate for the particulate; thus, a particulate is retained either on the surface of the porous medium or within the pores of the porous medium.

A class of particulates is selectively retained on a substrate if it is retained with greater affinity in comparison with another class of particulates. A class of particulates is not selectively retained if it is retained with the same or lesser affinity than another class of particulates, even if the class of particulates is retained on the substrate with some affinity.

A class of particulates is selectively eluted from the substrate if it is eluted from the substrate to a greater extent than another class of particulates, even if that other class of particulates is eluted from the substrate to some extent.

For ease of reference, the upstream surface of a porous medium is the surface initially contacted with the blood product, while the downstream surface is the other side, e.g., the side through which permeate is initially discharged.

The present invention provides a method of harvesting rare cells from blood products. The method involves first contacting a blood product containing rare cells with a porous medium wherein rare cells of interest are selectively retained on the porous medium. Subsequently, the porous medium is contacted with an elution fluid wherein a population of the rare cells of interest is eluted from the porous medium. Embodiments of the method include separating rare cells into distinct populations of cells.

The present inventive method involves first contacting a blood product containing rare cells with a porous medium. An appropriate blood product is any blood product having rare cells; suitable blood products can comprise other components as well (such as erythrocytes, platelets, and non-cellular particulate matter, or other products). One preferred blood product, however, is whole blood as it represents a readily available source of rare cells. Thus, for isolating many types of leukocytes, donated blood from blood banks is preferred, as it is plentiful and inexpensive. For isolating stem cells, a preferred blood product is blood drawn from an umbilicus.

The blood product containing rare cells is contacted with a porous medium such that the rare cells of interest are selectively retained on (including on the surface of or within the pores of) the porous medium. Any means of selectively retaining rare cells of interest on the porous medium is appropriate for use within the present inventive method.

For example, the blood product can be passed through the porous medium, or directed tangentially across the upstream surface of the medium, e.g., to allow a portion or component of the blood product to pass through the medium. Preferably, the porous medium is interposed into the pathway of fluid blood product such that the porous medium permits blood components which are not of interest, (e.g., fluids, erythrocytes, small particles, etc.) to pass through the porous medium. Thus, a pressure gradient is established through the porous medium, whereby the upstream pressure exceeds the downstream pressure, thereby promoting passage of the fluid phase, as well as particulate matter not retained on the porous medium, through the porous medium. Matter unable to traverse the porous medium is retained on the porous medium. Most of this matter (e.g., rare cells) is selectively retained on the porous medium. While pressure gradients of varying degrees can be established through the porous medium, preferably the pressure is not so great as to damage the rare cells retained on the porous medium.

Blood product components other than rare cells of interest (e.g., such as the liquid phase, blood-borne proteins, other macromolecules, and plentiful cells such as erythrocytes and platelets) are not selectively retained on the porous medium. Moreover, in some applications, sub-populations of rare cells are also not selectively retained on the porous medium (i.e., not all rare cells need be rare cells of interest). Thus, in accordance with the present inventive method, the porous medium can selectively retain any population of rare cells, such as, for example, a population including all rare cells, or any class, sub-population, or sub-group of rare cells (e.g., only rare cells of a given type).

Desirably, components of the blood product other than the rare cells of interest are not retained on the porous medium to nearly the extent as are the rare cells of interest (i.e., only the rare cells of interest are selectively retained on the porous medium). However, relatively minor amounts of these other components of the blood product, possibly including rare cells other than those of interest, can sometimes (but not preferably) be retained on the porous medium. Moreover, the porous medium can be substantially cleared of blood products other than the rare cells of interest by flushing the porous medium with a non-blood solution, such that the rare cells of interest are not thereby substantially removed from the porous medium.

As the rare cells of interest are selectively retained on the porous medium, the blood product fraction which passes through the porous medium (i.e., the effluent blood product) desirably does not include appreciable numbers of rare cells of interest. The effluent blood product, however, can include appreciable numbers of other rare cells (i.e., rare cells other than rare cells of interest).

Any type of porous medium is appropriate for use within the present inventive method, so long as the rare cells of interest are selectively retained on the porous medium as described herein. However, porous media for use in the present inventive method have at least two surfaces (i.e., a first or upstream surface and a second or downstream surface). Thus, for example, the porous medium can have any suitable pore structure and surface characteristics such that the porous medium selectively retains the rare cells of interest. Thus, the porous medium has a pore structure (e.g., a pore diameter) and surface characteristics sufficient to permit the fluid phase, erythrocytes, and macromolecules to selectively pass through the porous medium, while selectively preventing the rare cells of interest from passing through the porous medium (e.g., through sieving and/or adsorption).

The porous medium can be fashioned from any appropriate substance, such as organic or inorganic material. Preferably, however, the porous medium comprises synthetic material such as a polymeric material. Examples of porous media suitable for use in the present inventive method include those media described in U.S. Pat. Nos. 4,880,548 and 4,925,572 and International Published Patent Applications WO96/11738, WO95/17236, WO94/17894. Such porous media are typically employed as blood filters for donated blood and blood products, and a variety of such porous media are commercially available, such as, for example the Pall® RC-100 or RCXL2 Leukocyte Removal Filters, the Pall® SQ-40S Blood Transfusion Filter, Pall® BPF4 filters, etc. For applications of the present inventive method in which amoeboid cells are to be selectively retained on the porous medium, the porous medium preferably includes polyamides or polyesters having alipathic or aromatic groups, such as those polymers recited in U.S. Pat. No. 4,255,267, and especially nylons (e.g., polyamides such as nylon 6, nylon 66, nylon 610, nylon 612, nylon 11, nylon 12, and copolyamides such as nylon (6+610) or nylon (6+66+610)), as sub-populations of amoeboid rare cells selectively adhere to such media in the presence of divalent cations (e.g., $Ca^{++}$).

The porous medium can be of any suitable configuration. Preferably the porous medium forms a fibrous web (such as a non-woven fibrous web), most preferably having a rough and irregular surface (rather than a smooth surface) to permit amoeboid cells (e.g., granulocytes) to more strongly adhere to the porous medium. The porous medium also can be modified, e.g., surface modified, in any suitable manner. For example, the porous medium can be charge modified to increase the selective retention of the rare cells of interest. Moreover, the surface of the porous medium can be conjugated to ligands having selective affinity for the rare cells of interest (e.g., antibodies having selective affinity for the rare cells of interest) in order to facilitate selective retention of the rare cells of interest to the porous medium.

As mentioned, the porous medium to which rare cells are selectively retained is contacted with an elution fluid such that a population of rare cells is eluted from the porous medium. The elution fluid can be any suitable fluid for removing the rare cells of interest from the porous medium such that a population of the cells remains viable. Thus, the chemical composition of the elution fluid is such that it is physiologically compatible with the population of rare cells. However, the elution fluid can differ substantially from the chemical composition of naturally occurring physiological solutions.

One physiological parameter in which elution solutions can vary is in tonicity (i.e., osmolarity of the elution fluid vis-à-vis the cytoplasmic osmolarity). Of course, in many applications, it is desirable to employ isotonic elution fluids in order to minimize stress to the rare cells of interest. However, in some applications, the elution fluid preferably is hypotonic to the cells, as such fluid facilitates elution of some cell types from the porous medium. In other applications, the solution can be hypertonic, as such a solution facilitates selective retention of certain cell types to the porous medium.

Another physiological parameter in which elution solutions can vary, depending upon the rare cell population of interest, is temperature. At colder temperatures, the activity of cellular proteins (e.g., enzymes controlling cellular physiology and interaction with the extracellular microenvironment) is reduced. Colder elution fluids retard cellular metabolism and physiology, thereby reducing or substantially eliminating cellular capacity to respond to external cues (such as activating factors or promoters of phagocytotic or migratory behavior). Moreover, by affecting proteins mediating interaction with extracellular microenvironment, colder elution fluids attenuate the degree to which the rare cells adhere to the porous medium. Therefore, very cold elution fluids (e.g., fluids between about 0° C. and about 15° C., more typically above about 4° C.) promote the elution of a majority (e.g., most or substantially all) of the rare cell types from the surface of the porous medium. Elution fluids applied at physiologically ambient temperatures (typically in the range of about 37° C.), however, do not diminish metabolic response to environmental cues or strength of binding to the porous media substrate. Thus, for example, at physiological temperatures, migratory cells (e.g., granulocytes and other amoeboid cells) and/or phagocytotic cells adhere more strongly to the porous medium through cellular movement which brings more cellular surface area into contact with the porous medium.

The elution fluid also can vary in its nutritional value for the cells. In some applications, the elution fluid is a buffered saline (such as an acid-citrate buffered saline, a phosphate buffered saline, etc.). However, in other applications, the elution fluid is a nutrient-rich fluid such as a culture solution. Nutrient-rich fluids can enhance the viability of eluted cells, and therefore enhance the overall efficiency of rare cell recovery. Any suitable culture solution is appropriate for use as an elution fluid in accordance with the present inventive method. Such solutions are well known in the art. Examples of preferred culture solutions for use as the elution fluid of the present inventive method are Basal Media Eagle (BME), $CO_2$-independent media, Dulbecco's Modified Eagle Media (D-MEM), Fischer's Media, Leibovitz's L-15 Media, McCoy's 5A Media, MCDB 131 Medium, Minimum Essential Media (MEM), RPMI Media (e.g., RPMI Media 1630 or 1640), and other suitable media.

The elution fluid can vary in other respects as well, such as pH, osmolality, electrolyte concentration, and other parameters, such that a population of rare cells of interest is eluted from the porous medium and remains viable following contact with the elution fluid. Moreover, the elution fluid can include additional elements as well, such as sugars, buffers (e.g., phosphate buffers, citrate buffers, etc.), serum products, cryoprotectants, or other additives. For example, the elution fluid can include copolymers (e.g., poloxymers, etc.) for inhibiting the adhesion of certain cells to the porous medium, polymers for increasing viscosity in order to minimize stress to eluted cells (e.g., dextran 40 or 70) and/or cryoprotectants (e.g., mixtures including dimethyl sulfoxide (DMSO)) to minimize stress to cells stored at freezing temperatures. Preferably, the elution fluid comprises sugars (e.g., mono-, di-, or polysaccharides). More preferably, and especially when stem cells are the cells of interest, such sugars are glucose, sucrose, d-galactose, d-mannose, methyl-α-d-glucose, methyl-α-d-galactose, methyl-α-d-mannose, etc. Of these, for selective yield of leukocytes, d-mannose is most preferred.

In other embodiments, the elution fluid can comprise physiologically active substances. Thus, the elution fluid can comprise inhibitors of cell activation (e.g., leukocyte inhibitors such as prostaglandin E, steroids, or non-steroid anti-inflammatory agents) to substantially reduce or prevent activation of the cells when exposed to processing conditions, e.g., high shear rates.

Alternatively, for selective elution of desired populations of cells, the elution fluid can include cellular activators. While the elution fluid can include a variety of other factors, preferably the elution fluid does not contain effective amounts of toxins or other compounds which diminish the viability or activity of the rare cells of interest. For optimally retaining cellular viability, the elution fluid preferably includes a protein supplement, such as a serum product (e.g., bovine serum albumin (BSA), or fetal calf serum (FCS)), or protein (e.g., albumin).

Thus, one preferred elution fluid for use in the context of the present inventive method comprises D-MEM supplemented with bovine serum albumin and acid citrate-dextrose (ACD). Preferably, the solution has a BSA or FCS concentration of about 10–20 wt. %, and more preferably about 12–18 wt. %, such as about 14–16 wt. % (e.g., about 15 wt. %). Of course, the elution fluid can have significantly more or less BSA or FCS as well. The elution fluid also preferably has an ACD concentration of about 5–15 wt. %, and more preferably about 7–13 wt. %, such as about 9–11 wt. % (e.g., about 10 wt. %). Of course, the elution fluid can have significantly more or less ACD as well.

In addition, the elution fluid desirably includes physiologically acceptable concentrations of cations. While the range of cationic concentrations which are physiologically acceptable vary according to the species of cation, such ranges are well known in the art. Preferably, the elution fluid comprises divalent cations, especially calcium (i.e., $Ca^{++}$), and the elution solution preferably does not include a chelating agent. The presence of divalent cations in the elution fluid facilitates the elution of non-amoeboid cells from amoeboid cells, depending upon the nature of the porous medium, as herein described. Preferably, the divalent cation is present in a physiologically ambient concentration (e.g., a concentration approaching that of blood). Thus, for example, where the divalent cation is calcium, it can be present at about 0.05–10 mM $Ca^{++}$ and more preferably about 0.5–5 mM $Ca^{++}$, such as about 0.75–3 mM $Ca^{++}$ (e.g., about 1–2 mM $Ca^{++}$), and the elution fluid most preferably comprises about 1.2 mM $Ca^{++}$. Of course, the elution fluid can have significantly greater or lesser divalent cation concentration than these recited ranges as well. Moreover, whereas for purposes of illustration the divalent cation is indicated herein as divalent calcium, the divalent cation can be any species of divalent cation (e.g., magnesium or a complex divalent cationic species).

While in contact with the elution fluid, a population of rare cells is eluted from the porous medium. While this population can include most or substantially all types of rare cells selectively retained on the porous medium, in some applications the population includes less than all types of rare cells selectively retained on the porous medium (i.e., a sub-population of the rare cells). Any suitable process for eluting the population of interest is within the scope of the present inventive method. Thus, for example, the rare cells of interest can be eluted by diffusion from the porous medium into the elution fluid.

Desirably, fluid pressure is applied to the cells selectively retained on the porous medium to facilitate their dissociation from the porous medium by creating shear forces on the cells relative to the porous medium. Thus, for example, the rare cells of interest can be eluted by agitating the porous medium within the elution fluid, by centrifugation, by passing the elution fluid tangentially across a surface (e.g., the upstream surface) of the medium, or by other suitable means. Preferably, the rare cells of interest are eluted from the porous medium by flushing the medium with the elution fluid by passing the fluid through the medium under sufficient pressure to establish a flow rate therethrough. The medium can be flushed in either direction (forward flushing being passing the elution fluid through the porous medium in a direction from the upstream side towards the downstream side, backflushing being the reverse). However, the medium more preferably is backflushed because the greater concentration of cells is generally on the upstream surface of the porous medium.

In some embodiments, recovery efficiency is further enhanced by forward-flushing the filter medium in combination with backflushing. Thus, after backflushing the medium with a volume of elution fluid, the medium can then be forward-flushed with a second volume of elution fluid.

The flushing can be accomplished at any suitable fluid flow rate, e.g., about 0.1–15 $L/min/m^2$, although flow rates significantly more or less than this range can be used. .For example, backflushing can be accomplished at a fluid flow rate of about 0.5–10 $L/min/m^2$, such as about 1–8 $L/min/m^2$; more preferably the flow rate is about 1.5–7 $L/min/m^2$, such as about 2–6 $L/min/m^2$ or even about 2.5–5 $L/min/m^2$ (e.g., about 3–4 L $ml/min/m^2$). The most preferable flow rate depends upon the viscosity and temperature of the elution fluid, the nature of the porous medium, and the composition of the population of cells for elution. Thus, in some applications, such as when more gentle treatment of the cells is desired, backflushing can be accomplished at a flow rate about 1–100 $ml/min/m^2$ (e.g., about 15–85 $ml/min/m^2$); more preferably the flow rate is about 30–70 $ml/min/m^2$ or even about 40–60 $ml/min/m^2$ (e.g., about 50 $ml/min/m^2$).

To measure the efficiency of harvesting rare cells from blood products, the relative populations of the rare cells of interest prior to harvesting and subsequent to harvesting are compared. Overall harvesting efficiency largely depends upon the composition (i.e., the rare cell types) of the rare cell population of interest, and any degree of harvest efficiency is within the scope of the present inventive method. In some applications, the relative population of the rare cells of interest (i.e., the segregation efficiency) can be at least about doubled or about tripled, and in some applications, the relative population can increase by at least about 5 times, or even by about 10 times, e.g., by at least about an order of magnitude. Moreover, significantly higher efficiencies of segregation (e.g., at least two or several orders of magnitude or more) are achieved by the present inventive method in some applications.

While the present inventive method can effectuate the isolation of all types of rare cells from the blood product, in some applications it is desirable to separate the rare cells into sub-populations (e.g., a first population, a second population, etc.). In accordance with the present inventive method, rare cells can be separated into any number of desired groups, types, populations or classes.

In some embodiments, sub-populations of rare cells can be segregated by repeatedly retaining and/or eluting cells as described herein. As mentioned, the effluent blood product (i.e., the blood product fraction which passes through the porous medium) can include appreciable numbers of rare cells (i.e., rare cells other than rare cells of interest selectively retained on the porous medium). Subsequently, the effluent blood product can be exposed to a second porous medium for selectively retaining rare cells of interest as herein described. Thus, several discrete sub-populations of rare cells can be segregated by repeated applications of the present inventive method seriatim.

Another technique for isolating sub-populations of rare cells is by exploiting the differences in life spans between rare cell populations. As discussed herein, the elution fluid preferably is a nutrient-rich medium, such as a tissue culture solution. Some cells adhering to the porous medium remain viable if the porous medium is incubated for a period of days in the nutrient-rich elution fluid. While certain cell types do not survive long in culture or in vivo (e.g., certain populations of granulocytes), other cell types (e.g., certain populations of lymphocytes) are typically long-lived. Thus, if the porous medium is incubated in the elution fluid several days prior to applying shear forces to the cells, only those cells capable of surviving for a period of days are viably eluted.

While some dead cells are also eluted by this method, techniques for separating viable cells from dead cells are well known in the art, as are techniques for selectively plating or culturing only viable cells. Moreover, in some applications, the presence of cells (other than the rare cells of interest) in the eluate is material only if such others cells are viable (e.g., to avoid exposing the rare cells of interest to agents secreted by the other cells). Thus, in some applications, the presence of some dead cells among the rare cells of interest is of no practical significance. However, while this technique achieves a cell separation, it can result in reduced viability even of longer-lived cells, thus reducing the overall efficiency of recovery. Thus, the selective viability technique of cell separation, while within the scope of the present inventive method, is not preferable for every application.

In other embodiments, sub-populations of rare cells are segregated by selective elution/retention. As mentioned, not all rare cells selectively retained on the porous medium need be eluted by contacting the porous medium with the elution fluid. Thus, while the present inventive method allows rare cells of most or all types to be eluted from the porous medium, in preferred embodiments, a first population of rare cells is selectively eluted as herein described, while a second population of rare cells remains selectively retained on the porous medium after contact with the elution medium.

Segregating populations of rare cells by selective elution/retention in accordance with the present inventive method can be effectuated by any suitable technique. For example the temperature of the elution fluid can mediate selective retention/elution of populations of rare cells from the porous medium. As mentioned herein, temperature affects both metabolic activity and rare cell binding affinity for porous medium substrate. Thus, while most rare cell types are eluted at very cold temperatures, fewer types are eluted at temperatures approaching physiologically ambient temperatures. At intermediate temperatures, metabolic activity can be somewhat slowed while binding strength remains relatively high. Thus, for selective elution of non-amoeboid cells, the temperature of the elution fluid is desirably about 0–40° C., preferably about 5–37° C., more preferably about 15–35° C. and most preferably at about ambient room temperature such as about 20–30° C. (e.g., about 25° C.). Of course, in some applications, the temperature of the elution fluid can be considerably higher, such as 45° C. or even about 50° C., provided the rare cells of interest remain viable.

Another technique for segregating sub-populations of rare cells is to use a factor for promoting the continued selective adhesion of a first sub-population of rare cells to the porous medium without preventing the selective elution of a second sub-population of rare cells from the porous medium. Any suitable factor for promoting such selective elution of the second sub-population is appropriate for use within the present inventive method. The nature of this factor depends to a large extent upon the properties of the rare cell sub-populations of interest. A most suitable factor is one which promotes a first sub-population to adhere more strongly to the porous medium in comparison with a second sub-population. Moreover, the factor can be employed in any suitable manner, such as included within the elution fluid, conjugated to the porous medium, or even supplied by a population of the rare cells themselves.

In some embodiments, for example, the fluid can comprise a suitable compound for promoting the continued selective adhesion of a first sub-population of rare cells to the porous medium, thereby permitting the selective elution of a second sub-population of rare cells from the porous medium. Thus, the fluid can comprise a substance which activates the first sub-population of rare cells (e.g., a population of granulocytes or other phagocytotic cells) to adhere more strongly to the porous medium in comparison with the second sub-population. Any suitable activating factor appropriate for increasing the selective affinity of a sub-population of cells for the porous medium is within the scope of the present inventive method. Which activating factors are appropriate necessarily depends upon the desired sub-population of rare cells for continued selective retention on the porous medium. For example, where the population of cells to be retained on the porous medium includes granulocytes, the activating factor can be molecules such as bacterial toxins, cytokines, products of the complement complex (C3a, C4a, C5a, etc.), hormone activating factors, or other factors, which are well known in the art to stimulate granulocyte migration and/or phagocytotic activity.

The elution fluid can also include divalent cations, as is mentioned herein as preferred where the fluid is an elution fluid. Because divalent cations selectively increase the affinity of amoeboid cells (e.g., granulocytes) for the porous medium, the presence of divalent cations in the fluid facilitates the selective retention of amoeboid cells to the porous medium, while lymphocytes, dendritic cells and other non-amoeboid rare cells are thereby selectively eluted from the porous medium. Of course, any other factor for promoting the selective retention on the porous medium of one sub-population of rare cells vis-à-vis another sub-population is within the scope of the present inventive method.

Where a fluid includes an activating factor (or other factor or component for promoting the continued selective retention of a population of the rare cells to the porous medium), the fluid preferably is contacted with the porous medium under conditions appropriate for inducing the selective retention. The nature of these conditions depends upon the type of cells desired for continued selective retention on the porous medium, and such conditions are well known in the art. Where the desired cells are granulocytes or other amoeboid cells, the porous medium can be bathed in a fluid prior to application of shear forces upon the cells. Preferably, the porous medium is bathed in the fluid including the activating factor such that the factor diffuses into the porous medium from the downstream surface (i.e., the surface opposite to that to which the rare cells are primarily retained). Thus, the activating factor diffuses though the porous medium to establish a concentration gradient. By virtue of their chemotaxic proclivity, the amoeboid cells, such as granulocytes, are thereby induced to migrate away from the upstream surface and into (and possibly through) the porous medium in the direction of the increasing gradient. As the adherent surface of the porous medium preferably is rough, the amoeboid cells achieve a stronger interaction with the porous medium in comparison with the non-amoeboid cells.

After a sufficient period of time, the porous medium is subjected to shear forces as herein described. As substantially less shear force is required to elute cells from the upstream surface of the medium as compared to those cells actively adhering to the medium (e.g., cells which have become embedded within the porous medium), the sub-population of rare cells not exhibiting chemotaxis (e.g., lymphocytes, dendritic cells, etc.) is selectively eluted, while the sub-population of rare cells exhibiting chemotaxis (e.g., granulocytes) is selectively retained on the porous medium. Depending upon the viscosity of the elution fluid and the nature of the sub-populations of rare cells, an optimal elution velocity selectively dislodges one sub-population from the porous medium without selectively dislodging the second sub-population. Alternatively, where a population of amoeboid cells migrates through the porous medium, the population can be eluted from the porous medium into the fluid on contact with the downstream surface of the porous medium either prior to, or subsequent to, elution of the rare cells of interest from the upstream surface of the porous medium as herein described.

In addition to being supplied within an extraneous fluid (such as the elution fluid or other fluid as herein described), factors for promoting the enhanced selective adhesion of a first sub-population of rare cells to the porous medium while permitting the elution of a second sub-population of rare cells from the porous medium can be part of the porous medium (such as being conjugated to the porous medium). For example, the porous medium can have a means for increasing the affinity of the porous medium for a particular cell type. Thus, polymeric materials can be employed (e.g., nylon) to which certain cell types (e.g., granulocytes) strongly adhere preferentially.

Alternatively, the porous medium can be conjugated to an antibody specific for the first sub-population of rare cells.

Furthermore, the porous medium can have a ligand to which the first sub-population of rare cells binds. The presence of this high-affinity binding agent prompts the first sub-population to adhere more strongly to the porous medium than the second sub-population (although both sub-populations are selectively retained vis-à-vis the remainder of the blood product, as herein described). As a result, the second sub-population is eluted from the porous medium under conditions of significantly less shear force than is required to elute the first sub-population, thereby permitting the separation of the sub-populations.

While, as discussed herein, factors promoting the selective adhesion of one cell type to the porous medium can be supplied in a fluid or conjugated to the porous medium, such factors also can be supplied by a sub-population of the rare cells selectively retained on the porous medium. Thus, for example, prior to contacting the porous medium containing the rare cells with the elution fluid, the porous medium can be first contacted with an activation fluid such that a first sub-population of rare cells is activated to secrete a biologically active factor to which a second sub-population of the cells reacts so as to cause the second sub-population to adhere to the porous medium to a different extent than the first sub-population adheres to the porous medium. This step takes advantage of physiological interactions between sub-populations of rare cells.

Thereafter the porous medium is contacted with the elution fluid wherein one sub-population of rare cells is selectively eluted from the porous medium. For example, the porous medium to which the rare cells are attached can be contacted with a solution containing a factor for inducing lymphocytes to release hormones, such as IL-2. As IL-2 activates granulocytes to exhibit greater phagocytic activity, the granulocytes selectively adhere to the porous medium with a greater affinity in comparison with the secreting cells. As a result, greater shear force is required to dislodge the granulocytes from the porous medium than is required to elute the secreting cells. Thus, the secreting cells such as lymphocytes can be selectively removed from the porous medium while other cells can be selectively retained.

As an alternative to techniques herein described for using a factor to promote differential selective binding affinities among discrete sub-populations of rare cells, sub-populations of rare cells can be separated by using a second porous medium. Specifically, rare cells can be separated by contacting the elution fluid containing rare cells (e.g., the eluate from backflushing the first porous medium as herein described) with the second porous medium whereby a first sub-population of rare cells is selectively retained to the second porous medium while a second sub-population is not so retained. This selective binding of cell types to the second porous medium is achieved by any suitable technique, such as those techniques described herein. Thus, for example, the physical properties of the porous medium can be such that a first sub-population is selectively retained to the second porous medium while a second sub-population is not selectively retained. Alternatively, the second porous medium can include an antibody or ligand which selectively binds a sub-population of interest (as herein described). The selective binding of one sub-population to the second porous medium also can be achieved by any other suitable method.

The techniques of using a second porous medium, employing selective elution/retention on a porous medium, exploiting differential viability, etc., can be combined to achieve even finer separation of rare cell sub-populations. For example, the elution fluid containing a first sub-population of rare cells, but not containing a second sub-population of rare cells selectively retained on the first porous medium, can be contacted with a second porous medium such that the first sub-population is separated into a third sub-population of rare cells selectively retained on the second porous medium, and a fourth sub-population not selectively retained on the second porous medium. Furthermore, granulocytes can be induced, as described, to move away from the upstream surface of the porous medium by chemotaxic amoeboid migration.

Alternatively, lymphocytes can be activated to release IL-2, which further increases the macrophage's affinity for the porous medium. Activated lymphocytes release macrophage migration inhibiting factor, which attenuates granulocyte migration, causing them to remain embedded within the porous medium. Furthermore, the rare cells can be thus processed while selectively retained to a porous medium to which one sub-population binds with greater affinity in comparison to a second sub-population, as herein described. Other combinations of the techniques described herein also afford the ability to separate rare cells into discrete sub-populations, and yet other techniques can be employed within the scope of the present inventive method.

The present inventive method, thus, can separate rare cells into discrete sub-populations of cells by a variety of means. The present inventive method can segregate rare cells into any sub-population consisting essentially of cells with desired properties. For example, the present inventive method can segregate rare cells into a sub-population of cells which secrete a desired, biologically active substance and a sub-population of cells which do not secrete the desired substance. Alternatively, the present method can segregate phagocytotic rare cells from non-phagocytotic cells, stem cells from non-stem cells, etc. Thus, in some applications, the first sub-population preferably consists essentially of pharmacologically important cells such as lymphocytes, stem cells, dendritic cells, or other cells. The second sub-population of cells, thus, preferably consists essentially of phagocytotic cells, or other cells such as granulocytes (e.g., neutrophils, basophils, eosinophils, etc.), monocytes (e.g., macrophages), natural killer (NK) cells, or other such cells. Most preferably, the first sub-population of rare cells is substantially free of cells from the second sub-population of cells.

To measure the efficiency of a given separation, the relative populations of a given rare cell type prior to separation and subsequent to separation are compared. Overall efficiency of a given scheme of rare cell sub-population separation largely depends upon the nature of the sub-populations of interest. Moreover, any degree of separation is within the scope of the present inventive method, such as those degrees of the segregation of rare cells mentioned elsewhere herein.

Rare cells of interest (including any separated sub-populations of rare cells) isolated in accordance with the present inventive method can be manipulated in any desired manner. Thus, for example, the cells can be transfected, infected, subcloned, lysed, labeled, transformed, or otherwise manipulated. Desirably, the present inventive method involves culturing the eluted population of rare cells in a culture solution. Any culture solution can be utilized in the context of the present inventive method, e.g., any culture solution capable of supporting the rare cell population of interest, such as those culture solutions described herein. The rare cells of interest are desirably cultured to isolate products of cellular metabolism, such as secreted molecules. Thus, for example, the present inventive method allows lymphocytes to be selectively cultured for harvesting interferon and other secreted products of lymphocyte metabolism.

The present invention further provides a method for obtaining products of rare cells without eluting them from the porous medium. The method involves first contacting a blood product containing rare cells with a porous medium and retaining a population of rare cells on the porous medium. Subsequently, the population of rare cells is cultured on the porous medium by contacting the porous medium with a nutrient-rich culture solution. Typically, the method also involves isolating the products of the rare cells from the culture solution.

A rare cell population of interest from the blood product is selectively retained on the porous medium by any appropriate method, such as described herein. Of course, the population of interest can include all types of rare cells, or any desired sub-population of rare cells, as herein described. The effluent blood product (i.e., the blood product fraction which passes through the porous medium), thus can include appreciable numbers of rare cells (i.e., rare cells other than the rare cell population of interest). The effluent blood product can thereafter be subsequently exposed to a second porous medium (or additional porous media) for selectively retaining a second rare cell population (or additional rare cell populations), as herein described.

Subsequently, the porous medium on which the population of rare cells is selectively retained is exposed to (e.g., bathed in) a culture solution. A suitable culture solution is one which supports the population of rare cells of interest. Examples of appropriate culture solutions are described herein, and still others are well known in the art. The most desirable culture solution, of course, depends to a large extent on the type of rare cells within the population of interest, and selection of a suitable culture solution is well known in the art.

Within the culture solution, the porous medium serves as a substrate for the rare cells of interest. Thus, any method for incubating the porous medium within the culture solution is appropriate. For example, the porous medium can be laid upon the surface of a culture dish containing the culture solution so as to wet the porous medium. Preferably, the porous medium is completely wetted, such as by being submerged within the culture solution. Thus, the rare cell population is cultured upon the porous medium. The rare cell population can be so cultured under any suitable conditions, which, of course, vary depending upon the nature of the culture solution (e.g., $CO_2$ concentration, pH, temperature, etc.). The incubation of cell cultures is well known in the art.

Any rare cell population of interest can be cultured in accordance with the present inventive method. Moreover, the population of interest can be a sub-population of rare cells, such as a sub-population of rare cells segregated as disclosed herein. A preferred rare cell population includes lymphocytes. While cultured upon the porous medium in accordance with the present inventive method, the lymphocytes can be activated to produce interferon, lymphokines, or other factors. Thus, where lymphocytes are cultured, the culture solution preferably contains a factor for activating lymphocytes. Any such activating factor is appropriate, and such factors are well known in the art. Thereafter, the culture medium is changed regularly for isolating the secreted factors.

The following examples further illustrate the present invention but, of course, should not be construed as in any way limiting its scope.

EXAMPLE 1

This example demonstrates that the present inventive method can selectively recover leukocytes (white blood cells) from blood products.

Standard units of packed red blood cells (PRCs) in Adsol™ additive solutions were obtained from blood donor centers accredited with the American Association of Blood Banks. On the day of experimentation, the packed PRCs were 2–7 days old. Prior to filtration, each unit was weighed, and the hemolotologic index (i.e., hematocrit, white cell contents, platelet concentration, etc.) was measured via an automated hematology analyzer.

Each unit of RBCs was connected to a Pall® BPF4 leukoreducing filter and then filtered. Filtrate effluent was collected in 600 ml plastic transfer bags.

Subsequent to filtration, the inlet tubing of each filter unit was clamped, and the filter removed from the blood bag. Following filter removal, the clamp was removed, and all but about 8 mm each of inlet and outlet tubing was removed from the filters.

A 60 ml syringe containing elution fluid (DMEM supplemented with 15 wt. % BSA or FCS, and 10 wt. % ACD formula A (i.e., 2.5 g/l dextrose, 2.20 g/l sodium citrate dihydrate, and 730 mg/l anhydrous citric acid) at about 4° C., was attached to the outlet tubing of the filter, and the filter was backflushed at a flow rate of about 2.5 L/min/m². In total, each filter was backflushed with several syringe volumes (i.e., about 280 ml) of elution fluid in order to elute substantially all residual erythrocytes from the filters. Subsequently, each filter was flushed with 120 ml of air in order to remove all residual elution fluid.

Following elution, each volume of elution fluid was weighed for volume determination (assuming a density of 1.0 g/ml), and the hemolotologic index was measured via an automated hematology analyzer. From the measurements, the leukocyte concentration prior to filtration and the concentration subsequent to elution were calculated, thereby providing a measurement of overall leukocyte recovery efficiency. These results are presented in Table 1.

TABLE 1

| | LEUKOCYTE RECOVERY | | |
|---|---|---|---|
| Unit | Starting Leukocyte Concentration ($10^9$ cells/unit) | Eluent Leukocyte Concentration ($10^9$ cells/unit) | Efficiency |
| 1 | 3.66 | 2.20 | 60.1% |
| 2 | 3.95 | 2.63 | 66.6% |
| 3 | 2.63 | 1.79 | 68.1% |
| Mean ± SD | 3.41 ± 0.69 | 2.21 ± 0.42 | 64.9 ± 4.2% |

These data demonstrate that the present inventive method effectively recovers about 65% of the leukocytes in a unit of PRC.

EXAMPLE 2

This example demonstrates that the present inventive method can selectively recover leukocytes.

Standard units of PRC obtained from blood banks were treated substantially as in Example 1 with the following exceptions. The PRCs were between 2 hours to 12 days old, as indicated in Table 2. To PRCs older than one day were added Adsol additive. The elution was performed by detaching the filter from the bags and attaching a flexible tube to the outlet port. The other end of the tube was attached to a peristaltic pump. Elution fluid was passed through the filters at different flow rates (indicated in Table 2). Moreover, in flushing the filters, the direction of the flow was reversed by stopping the pump, removing the filters from the tube, attaching the tube to the other filter port, and restarting the pump. The amount of elution fluid sent through the filters in each direction is indicated in Table 2.

Two elution fluids, "A" (experimental) and "C" (control) were employed in the experiments. Both solutions were 30 g/L human albumin, 0.01 M $K_2PO_4$, and 0.15 M NaCl. In addition, solution "A" included 90 g/L Dextran (mw=66–70,000), 3.0 mM EDTA, and 10 g/L Pluronic F68 copolymer. Some experiments were conducted with cold elution fluid (22±2° C.) while others were conducted with warm elution fluid (37±2° C.). Eluted white blood cells (Wbcs) were collected in sterile 250 ml centrifuge tubes and the cell count, as well as other hematological indicators, was measured as indicated in Example 1.

The percent recovery for each of the samples is reported in Table 2.

complex. The filters are incubated with the outflow surface in contact with the elution fluid for 1 hour at about room temperature. Subsequently, the filters are backflushed as previously described.

Substantially more non-amoeboid leukocytes are eluted from the filters when the filters are exposed to factors known to promote granulocyte chemotaxis.

EXAMPLE 4

This example demonstrates that the present inventive method can selectively recover mononuclear cells (monocytes and lymphocytes)

Fresh units of human whole blood in Citrate Phosphate Dextrose (CPD) anticoagulant were obtained. About 90–100 mL aliquots of blood were filtered through Pall® Purecell-Neo or Pall® BPF4 leukoreducing filters. Filtrate effluent was collected in separate plastic transfer bags.

TABLE 2

| Sample ID | Age of blood | Type of solution | Influent Vol. (ml) | Influent Wbc ct | Effluent Vol/(ml) | Effluent Wbc ct | % recovery |
|---|---|---|---|---|---|---|---|
| 1 | fresh PRC | C cold | 320 | 5400 | 275 | 1600 | 25.5 |
| 2 | 12 days | A cold | 355 | 2750 | 225 | 2100 | 48.4 |
| 3 | 12 days | A cold | 329 | 5500 | 225 | 3800 | 47.3 |
| 4 | 12 days | A cold | 333 | 2500 | 250 | 2500 | 75.1 |
| 5 | 5 days | A warm | 346 | 8850 | 225 | 7700 | 56.6 |
| 6 | 5 days | A warm | 347 | 5200 | 225 | 3500 | 43.6 |
| 7 | 5 days | A cold | 402 | 5150 | 250 | 1600 | 19.3 |
| 8 | 5 days | A cold | 386 | 9150 | 230 | 4700 | 30.6 |
| 9 | 5 days | A warm | 361 | 5650 | 235 | 8350 | 96.2 |

Sample #1 - Flow rate 200 ml/min. Reverse - 100 ml, Forward - 100 ml, Reverse - 75 ml.
Sample #2 - Flow rate 225 ml/min. Reverse - 100 ml, Forward - 125 ml (flow rate 250 ml/min.)
Sample #3 - Flow rate 300 ml/min. Reverse - 125 ml, Forward - 100 ml.
Sample #4 - Flow rate 400 ml/min. Reverse - 100 ml, Forward - 150 ml.
Samples #5–8 - Flow rate 400 ml/min. Reverse - 125 ml, Forward - balance of effluent volume.
Sample #9 - Flow rate 450 ml/min. Reverse - 125 ml, Forward - balance of effluent volume.

EXAMPLE 3

This example demonstrates that the present inventive method can selectively recover one sub-population of leukocytes from another sub-population.

Filters are obtained and treated as in Example 1 with the following exceptions. Prior to backflushing and removing the clamp, the short outflow tube segment is filled with elution fluid to which has been added cytokines (notably IL-2) and the C3a, C4a, and C5a products of the complement After filtration, the filters were backflushed with 259 mL of an elution fluid containing buffered 9% (w/v) Dextran 70 (m.w. 70,000), 3–5% human albumin, 2–5% (w/v) sucrose, 0.01M potassium phosphate and 0.15M sodium chloride, at a flow rate of about 300–400 mL/minute.

The results are presented in Table 3 (Pall® PurecellNeo) and Table 4 (Pall® BPF4)

TABLE 3

Recovery of mononuclear cells from Pall ® Purecell Neo leukocyte reducing filters

| Filter Type | Volume of Blood Filtered (mL) | Volume of Cells Recovered (mL) | Concentration of MNC In blood (cells/µL) | Concentration of MNC Recovered (cells/µL) | Recovered MNC (%) |
|---|---|---|---|---|---|
| Purecell Neo | 95.1 | 250 | 2,050 | 800 | 100 |
| Purecell Neo | 96.9 | 250 | 2,050 | 750 | 94.4 |
| Purecell Neo | 96.5 | 250 | 2,050 | 850 | 100 |
| Purecell Neo | 94.5 | 250 | 2,050 | 850 | 100 |

TABLE 4

Recovery of mononuclear cells from Pall ® BPF4 leukocyte reducing filters

| Filter Type | Volume of Blood Filtered (mL) | Volume of Cells Recovered (mL) | Concentration of MNC In blood (cells/μL) | Concentration of MNC Recovered (cells/μL) | Recovered MNC (%) |
|---|---|---|---|---|---|
| BPF4 | 95.9 | 250 | 1,200 | 400 | 86.9 |
| BPF4 | 94.9 | 250 | 1,200 | 400 | 88.2 |
| BPF4 | 99.6 | 250 | 1,200 | 400 | 83.7 |
| BPF4 | 95.7 | 250 | 1,200 | 500 | 100 |
| BPF4 | 97.8 | 250 | 1,200 | 400 | 85.2 |
| BPF4 | 95.7 | 250 | 1,200 | 700 | 82.7 |
| BPF4 | 95.3 | 250 | 1,200 | 750 | 85.5 |
| BPF4 | 99.4 | 250 | 1,200 | 800 | 87.5 |
| BPF4 | 94.9 | 250 | 1,200 | 700 | 80.2 |

These data demonstrate that the present inventive method effectively recovers about 80–100% of the mononuclear cells (MNC) present in an aliquot of whole blood.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of harvesting rare cells from a blood product comprising:
   contacting a blood product containing rare cells with a porous medium comprising a fibrous web;
   selectively retaining said rare cells on said porous medium;
   contacting said porous medium with a nutrient-rich elution fluid including a viscosity increasing polymer comprising dextran; and
   selectively eluting said rare cells from said porous medium.

2. The method of claim 1, wherein said elution fluid further comprises Dulbecco's Modified Eagles Medium supplemented with bovine serum albumin and acid citrate-dextrose.

3. The method of claim 1, wherein contacting the porous medium with the elution fluid comprises backflushing the porous medium with the elution fluid.

4. The method of claim 1, wherein said blood product includes at least first and second populations of rare cells, wherein the first population of rare cells is selectively eluted and the second population of rare cells remains selectively retained on the porous medium after contact with said elution fluid.

5. The method of claim 4, wherein said second population consists essentially of dendritic cells, granulocytes, monocytes, macrophages, or stem cells.

6. The method of claim 4, wherein said elution fluid promotes the selective adhesion of said second population of rare cells to said porous medium.

7. The method of claim 4, wherein said elution fluid comprises a divalent cation.

8. The method of The method of claim 4, wherein said elution fluid comprises a cytokine.

9. The method of claim 4, wherein said elution fluid comprises at least one complement complex product.

10. The method of claim 9, wherein said complement complex product is selected from the group consisting of C3a, C4a, and C5a.

11. The method of claim 1, wherein said rare cells comprise lymphocytes.

12. The method of claim 11, further comprising culturing the lymphocytes.

13. The method of claim 1, wherein said rare cells comprise stem cells.

14. The method of claim 1, wherein the rare cells comprise leukocytes.

15. The method of claim 1, further comprising culturing the eluted rare cells.

16. The method of claim 11, further comprising culturing the lymphocytes.

17. The method of claim 14, further comprising culturing the leukocytes.

18. The method of claim 13, further comprising culturing the stem cells.

19. The method of claim 14, wherein the elution fluid further comprises albumin and at least one additional sugar.

20. The method of claim 1, wherein the rare cells are dendritic cells and the method further comprises culturing the dentritic cells.

21. The method of claim 1, wherein the rare cells are mononuclear cells.

22. A method of harvesting rare cells from a blood product comprising:
   contacting a blood product containing said rare cells with a porous medium comprising a fibrous web;
   selectively retaining said rare cells on said porous medium;
   contacting said porous medium with an elution fluid at a temperature of between about 5–37° C., wherein said elution fluid includes a viscosity increasing polymer comprising dextran; and
   selectively eluting said rare cells from said porous medium.

23. The method of claim 22, wherein said elution fluid comprises at least one additional sugar.

24. The method of claim 22, wherein said elution fluid further comprises buffered saline.

25. The method of claim 22, wherein said elution fluid is at a temperature of between about 15–35° C.

26. The method of claim 25, wherein said elution fluid is at a temperature of between about 20–30° C.

27. The method of claim 22, wherein the blood product includes at least first and second populations of rare cells, wherein the first population of rare cells is selectively eluted and wherein the second population of rare cells remains selectively retained on the porous medium after contact with said elution fluid.

28. The method of claim 27, wherein said first population consists essentially of lymphocytes.

29. The method of claim 22, wherein said rare cells comprise lymphocytes.

30. The method of claim 22, wherein said rare cells comprise stem cells.

31. The method of claim 22, further comprising culturing the eluted rare cells.

32. The method of claim 29, further comprising culturing the lymphocytes.

33. The method of claim 22, wherein the rare cells comprise leukocytes.

34. The method of claim 33, further comprising culturing the leukocytes.

35. The method of claim 30, further comprising culturing the stem cells.

36. The method of claim 33, wherein the elution fluid further comprises albumin and at least one additional sugar.

37. The method of claim 22, wherein the rare cells are dendritic cells and the method further comprises culturing the dendritic cells.

38. The method of claim 22, wherein the rare cells are mononuclear cells.

39. The method of claim 22, wherein contacting the porous medium with the elution fluid comprises backflushing the porous medium with the elution fluid.

40. A method of harvesting rare cells comprising stem cells from a blood product comprising:
contacting a blood product containing said rare cells comprising stem cells with a porous medium;
selectively retaining said stem cells on said porous medium;
backflushing said porous medium with a nutrient-rich elution fluid at a temperature of between about 5–37° C., wherein said elution fluid includes a viscosity increasing polymer; and
selectively eluting said stem cells from said porous medium.

41. The method of claim 40, wherein the porous medium comprises a fibrous web.

42. The method of claim 40, further comprising culturing the eluted stem cells.

43. The method of claim 40, further comprising culturing the stem cells.

44. The method of claim 40, wherein the elution fluid further comprises albumin and at least one additional sugar.

45. The method of claim 40, wherein the viscosity increasing polymer comprises dextran.

46. A method of harvesting rare cells from a blood product comprising:
contacting a blood product containing rare cells comprising dendritic cells with a porous medium comprising a fibrous web;
selectively retaining said dendritic cells on said porous medium;
contacting said porous medium with an elution fluid at a temperature of between about 5–37° C., wherein said elution fluid includes a viscosity increasing polymer;
selectively eluting said dendritic cells from said porous medium; and
culturing the dendritic cells.

47. The method of claim 46, wherein contacting the porous medium with the elution fluid comprises backflushing the porous medium with the elution fluid.

48. A method of harvesting rare cells from a blood product comprising:
contacting a blood product containing rare cells comprising dendritic cells with a porous medium;
selectively retaining said dendritic cells on said porous medium;
contacting said porous medium with a nutrient-rich elution fluid including a viscosity increasing polymer;
selectively eluting said dendritic cells from said porous medium; and,
culturing the dendritic cells.

49. A method of harvesting rare cells from a blood product comprising:
contacting a blood product including at least first and second populations of rare cells with a porous medium;
selectively retaining said second population of rare cells on said porous medium;
contacting said porous medium with a nutrient-rich elution fluid comprising a viscosity increasing polymer and a cytokine; and
selectively eluting said first population of rare cells from said porous medium.

50. A method of harvesting rare cells from a blood product comprising:
contacting a blood product including at least first and second populations of rare cells with a porous medium;
selectively retaining said second population of rare cells on said porous medium;
contacting said porous medium with a nutrient-rich elution-fluid comprising a viscosity increasing polymer and at least one complement complex product; and
selectively eluting said first population of rare cells from said porous medium.

51. The method of claim 50, wherein said complement complex product is selected from the group consisting of C3a, C4a, and C5a.

52. A method of harvesting rare cells from a blood product comprising:
contacting a blood product containing rare cells comprising leukocytes with a porous medium comprising a fibrous web;
selectively retaining said rare cells on said porous medium;
backflushing said porous medium with a nutrient-rich elution fluid including a viscosity increasing polymer comprising dextran; and
selectively eluting said rare cells from said porous medium.

* * * * *